(12) United States Patent
Lim et al.

(10) Patent No.: US 7,862,590 B2
(45) Date of Patent: Jan. 4, 2011

(54) INTERSPINOUS PROCESS SPACER

(75) Inventors: Roy Lim, Germantown, TN (US);
Michael C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 72 days.

(21) Appl. No.: 11/102,396

(22) Filed: Apr. 8, 2005

(65) Prior Publication Data

US 2006/0241610 A1 Oct. 26, 2006

(51) Int. Cl.
*A61B 17/70* (2006.01)
(52) U.S. Cl. .................................. 606/248; 623/17.11
(58) Field of Classification Search ... 623/16.11–17.16; 606/61, 246–249
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,570,618 A * | 2/1986 | Wu | 606/61 |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 5,011,484 A | 4/1991 | Breard | |
| 5,047,055 A | 9/1991 | Bao et al. | |
| 5,092,866 A | 3/1992 | Breard et al. | |
| 5,201,734 A | 4/1993 | Cozad et al. | |
| 5,306,275 A | 4/1994 | Bryan | |
| 5,360,430 A | 11/1994 | Lin | |
| 5,366,455 A * | 11/1994 | Dove et al. | 606/61 |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,527,312 A * | 6/1996 | Ray | 606/61 |
| 5,609,634 A * | 3/1997 | Voydeville | 623/13.11 |
| 5,628,756 A | 5/1997 | Barker, Jr. et al. | |
| 5,645,599 A | 7/1997 | Samani | |

(Continued)

FOREIGN PATENT DOCUMENTS

DE   2821678 A1   11/1979

(Continued)

OTHER PUBLICATIONS

"Dispositivo Intervertebrale Ammortizzante DIAM," date unknown, p. 1.

(Continued)

*Primary Examiner*—Eduardo C Robert
*Assistant Examiner*—Tara R George
(74) *Attorney, Agent, or Firm*—Coats and Bennett, P.L.L.C.

(57) ABSTRACT

Embodiments of an interspinous spacer that maintains spacing between a superior vertebra and inferior vertebra following a laminectomy. The interspinous spacer may include a superior arch engaging the spinous process of a superior vertebra and an inferior arch engaging the spinous process of an inferior vertebra. The superior arch and inferior arch may define a central opening in the interspinous spacer.

16 Claims, 10 Drawing Sheets

U.S. PATENT DOCUMENTS

| | | | |
|---|---|---|---|
| 5,674,295 | A | 10/1997 | Ray et al. |
| 5,676,702 | A | 10/1997 | Ratron |
| 5,690,649 | A | 11/1997 | Li |
| 5,810,815 | A | 9/1998 | Morales |
| 5,836,948 | A * | 11/1998 | Zucherman et al. ......... 606/249 |
| 5,860,977 | A | 1/1999 | Zucherman et al. |
| 5,976,186 | A | 11/1999 | Bao et al. |
| 6,022,376 | A | 2/2000 | Assell et al. |
| 6,048,342 | A | 4/2000 | Zucherman et al. |
| 6,068,630 | A | 5/2000 | Zucherman et al. |
| 6,132,464 | A * | 10/2000 | Martin ................... 623/17.15 |
| 6,293,949 | B1 | 9/2001 | Justis et al. |
| 6,352,537 | B1 | 3/2002 | Strnad |
| 6,364,883 | B1 | 4/2002 | Santilli |
| 6,402,750 | B1 | 6/2002 | Atkinson et al. |
| 6,440,169 | B1 | 8/2002 | Elberg et al. |
| 6,451,019 | B1 | 9/2002 | Zucherman et al. |
| 6,565,605 | B2 * | 5/2003 | Goble et al. ............. 623/17.11 |
| 6,582,433 | B2 | 6/2003 | Yun |
| 6,626,909 | B2 | 9/2003 | Chin |
| 6,626,944 | B1 * | 9/2003 | Taylor ................... 623/17.16 |
| 6,645,207 | B2 | 11/2003 | Dixon et al. |
| 6,669,729 | B2 | 12/2003 | Chin |
| 6,695,842 | B2 | 2/2004 | Zucherman et al. |
| 6,709,435 | B2 | 3/2004 | Lin |
| 6,723,126 | B1 | 4/2004 | Berry |
| 6,733,534 | B2 | 5/2004 | Sherman |
| 6,761,720 | B1 | 7/2004 | Senegas |
| 6,835,205 | B2 | 12/2004 | Atkinson et al. |
| 6,946,000 | B2 | 9/2005 | Senegas et al. |
| 7,041,136 | B2 | 5/2006 | Goble et al. |
| 7,048,736 | B2 | 5/2006 | Robinson et al. |
| 7,087,083 | B2 | 8/2006 | Pasquet et al. |
| 7,163,558 | B2 | 1/2007 | Senegas et al. |
| 7,201,751 | B2 | 4/2007 | Zucherman et al. |
| 7,238,204 | B2 | 7/2007 | Le Couedic et al. |
| 7,282,064 | B2 * | 10/2007 | Chin ..................... 623/17.15 |
| 7,306,628 | B2 | 12/2007 | Zucherman et al. |
| 7,442,208 | B2 | 10/2008 | Mathieu et al. |
| 7,445,637 | B2 | 11/2008 | Taylor |
| 2002/0029039 | A1 * | 3/2002 | Zucherman et al. ........... 606/61 |
| 2003/0028250 | A1 | 2/2003 | Reiley et al. |
| 2003/0153915 | A1 | 8/2003 | Nekozuka et al. |
| 2003/0163162 | A1 | 8/2003 | Uehara et al. |
| 2003/0171750 | A1 | 9/2003 | Chin |
| 2004/0015166 | A1 | 1/2004 | Gorek |
| 2004/0049272 | A1 * | 3/2004 | Reiley ................... 623/17.11 |
| 2004/0097931 | A1 | 5/2004 | Mitchell |
| 2004/0158245 | A1 | 8/2004 | Chin |
| 2004/0172024 | A1 | 9/2004 | Gorek |
| 2004/0236327 | A1 | 11/2004 | Paul et al. |
| 2004/0243239 | A1 * | 12/2004 | Taylor ................... 623/17.13 |
| 2005/0010293 | A1 | 1/2005 | Zucherman et al. |
| 2005/0033434 | A1 * | 2/2005 | Berry ..................... 623/17.14 |
| 2005/0049704 | A1 * | 3/2005 | Jackson ................. 623/17.11 |
| 2005/0049708 | A1 | 3/2005 | Atkinson et al. |
| 2005/0165398 | A1 | 7/2005 | Reiley |
| 2005/0203512 | A1 | 9/2005 | Hawkins et al. |
| 2005/0203624 | A1 | 9/2005 | Serhan et al. |
| 2005/0228391 | A1 | 10/2005 | Levy et al. |
| 2005/0245929 | A1 * | 11/2005 | Winslow et al. ............... 606/61 |
| 2005/0261768 | A1 | 11/2005 | Trieu |
| 2005/0288672 | A1 | 12/2005 | Ferree |
| 2006/0004447 | A1 | 1/2006 | Mastrorio et al. |
| 2006/0015181 | A1 | 1/2006 | Elberg |
| 2006/0064165 | A1 | 3/2006 | Zucherman et al. |
| 2006/0084983 | A1 | 4/2006 | Kim |
| 2006/0084985 | A1 | 4/2006 | Kim |
| 2006/0084987 | A1 | 4/2006 | Kim |
| 2006/0084988 | A1 | 4/2006 | Kim |
| 2006/0085069 | A1 | 4/2006 | Kim |
| 2006/0089654 | A1 | 4/2006 | Lins et al. |
| 2006/0089719 | A1 | 4/2006 | Trieu |
| 2006/0106381 | A1 | 5/2006 | Ferree et al. |
| 2006/0106397 | A1 | 5/2006 | Lins |
| 2006/0111728 | A1 | 5/2006 | Abdou |
| 2006/0122620 | A1 | 6/2006 | Kim |
| 2006/0136060 | A1 | 6/2006 | Taylor |
| 2006/0184247 | A1 | 8/2006 | Edidin et al. |
| 2006/0184248 | A1 | 8/2006 | Edidin et al. |
| 2006/0195102 | A1 | 8/2006 | Malandain |
| 2006/0217726 | A1 | 9/2006 | Maxy et al. |
| 2006/0241757 | A1 | 10/2006 | Anderson |
| 2006/0264938 | A1 | 11/2006 | Zucherman et al. |
| 2006/0271044 | A1 | 11/2006 | Petrini et al. |
| 2006/0293662 | A1 | 12/2006 | Boyer, II et al. |

FOREIGN PATENT DOCUMENTS

| | | |
|---|---|---|
| EP | 0322334 B1 | 2/1992 |
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 A1 | 5/2002 |
| FR | 2822051 A1 | 9/2002 |
| FR | 2850009 A1 | 7/2004 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2007/034516 A1 | 3/2007 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Aota et al., "Postfusion Instability at the Adjacent Segments After Rigid Pedicle Screw Fixation for Degenerative Lumbar Spinal Disorders," J. Spinal Dis., Dec. 1995, pp. 464-473, vol. 8, No. 6.

Benzel et al., "Posterior Cervical Interspinous Compression Wiring and Fusion for Mid to Low Cervical Spinal Injuries," J. Neurosurg., Jun. 1989, pp. 893-899, vol. 70.

Booth et al., "Complications and Predictive Factors for the Successful Treatment of Flatback Deformity (Fixed Sagittal Imbalance)," SPINE, 1999, pp. 1712-1720, vol. 24, No. 16.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertebral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societá di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rahm et al., "Adjacent-Segment Degeneration After Lumbar Fusion with Instrumentation: A Retrospective Study," J. Spinal Dis., Oct. 1996, pp. 392-400, vol. 9, No. 5.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schären et al, "Erfolge and Probleme langstreckiger Fusionen der degenerativen Lendenwirbelsäule," Osteosynthese International, Jul. 17, 1998, pp. 173-179, vol. 6, Johann Ambrosius Barth.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "Lumbar Motion Segment Pathology Adjacent to Thoracolumbar, Lumbar, and Lumbosacral Fusions," SPINE, Apr. 15, 1996, pp. 970-981, vol. 21, No. 8.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expéience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

INTERSPINOUS PROCESS SPACER

BACKGROUND

The laminae are a part of the posterior arch of the vertebrae. The laminae comprise two flattened plates that extend medially from the pedicles and meet at the spinous process to form the posterior wall of the spinal foramen. A laminectomy is a procedure to remove all or part of the lamina and spinous process. This procedure is commonly performed to remove an intervertebral disc, or to decompress a nerve root. Following a decompression laminectomy, a spinal fusion is typically required to stabilize the spine, which results in some loss of mobility. There is therefore a need for a prosthetic device that can stabilize the spine following a laminectomy while maintaining some degree of flexibility.

SUMMARY

Embodiments of an interspinous spacer that maintains spacing between a superior vertebra and inferior vertebra following a laminectomy. The interspinous spacer may include a superior arch engaging the spinous process of a superior vertebra and an inferior arch engaging the spinous process of an inferior vertebra. The superior arch and inferior arch may define a central opening in the interspinous spacer. In one exemplary embodiment, the superior arch and inferior arch may be provided with a saddle to receive the spinous processes of the adjacent superior and inferior vertebrae. Tethers may retain the spinous processes of the adjacent vertebra in the saddles.

In another exemplary embodiment, anchor plates may be disposed at the junction of the superior and inferior arches of the interspinous spacer for attaching the interspinous spacer to the pedicles of the compromised vertebra. The anchor plates may include openings for pedicle screws. The pedicle screws may pass through the openings in the anchor plates and thread into the pedicles to secure the interspinous spacer to the pedicles. Alternatively, or in addition, the interspinous spacer may include tethers that loop around the transverse processes of the compromised vertebra. A second set of tethers may pass around the spinous processes of the adjacent superior and inferior vertebrae.

DETAILED DESCRIPTION

Figure 1:
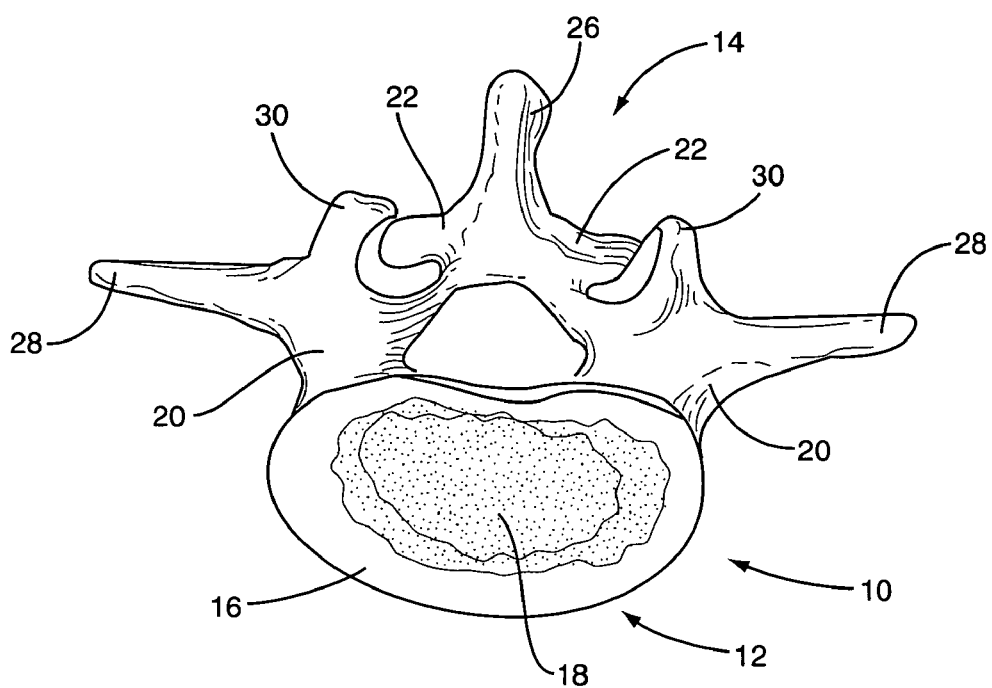
FIG. 1 illustrates a vertebra as seen from above.
Figure 2:
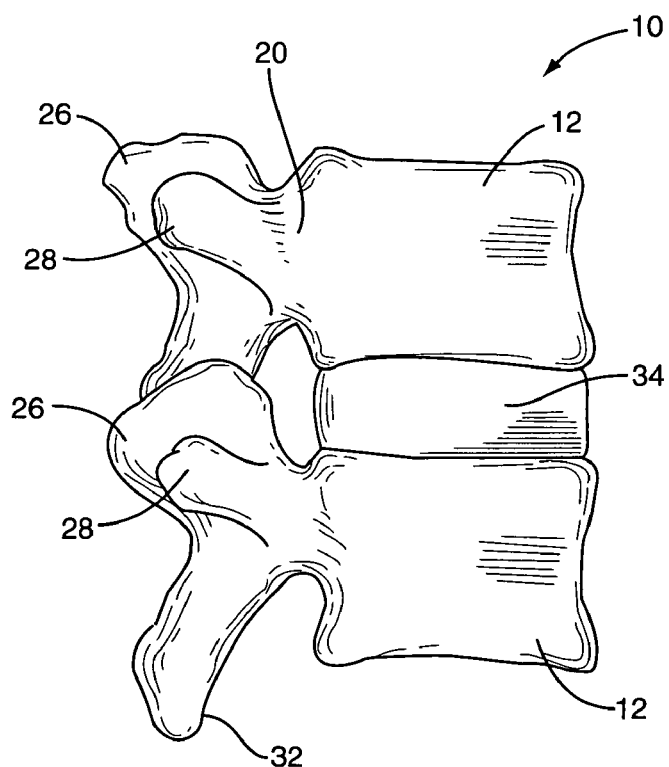
FIG. 2 illustrates two adjacent vertebrae as seen from one side.

FIGS. 1 and 2 illustrate the structure of a vertebra indicated generally by the numeral 10. The vertebra 10 comprises vertebral body 12 and a vertebral arch 14. The vertebral body 12 comprises a dense ring of cortical bone 16 surrounding cancellous bone 18. The vertebral arch comprises the pedicles 20 and laminae 22, which together form an arch, and various spinal processes 26-32 that provide attachment points for ligaments and tendons. The pedicles 20 extend posteriorly from the lateral margins of the vertebral body 12. The laminae 22 extend medially from the pedicles 20 and form the posterior wall of the spinal foramen 24. The spinal processes include the spinous process 26, two transverse processes 28, and four articular processes 30, 32. The spinous process 26 extends posteriorly form the junction of the laminae 22. The transverse processes 28 extend laterally from respective pedicles. The superior articular processes 30 and inferior articular processes 32 extend from the junction of the pedicles 20 and laminae 22. The superior articular processes 30 of one vertebra 10 join with the inferior articular processes 32 of an adjacent vertebra 10 to form articulating joints called facet joints. The facet joints work in combination with the intervertebral disc 34 to allow relative movement of the vertebrae 10.

Figure 3:
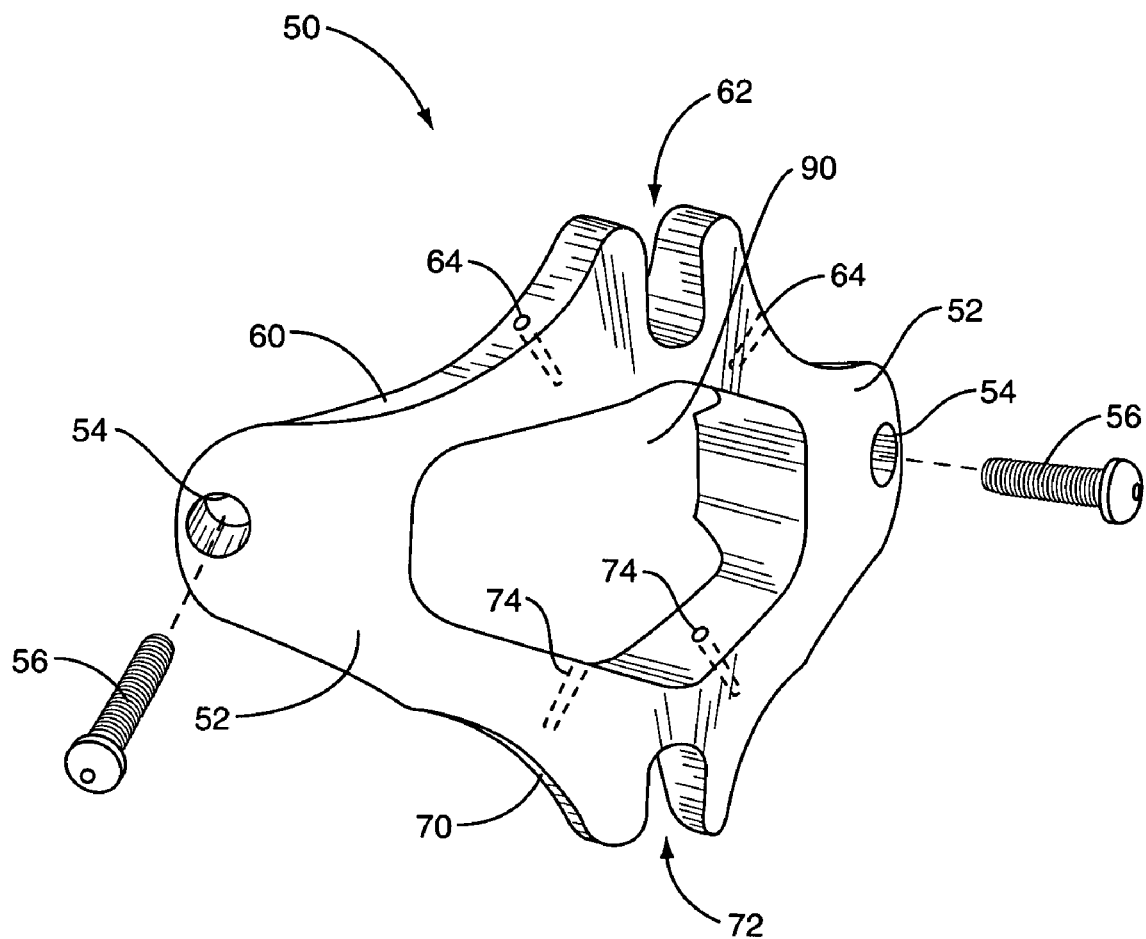
FIG. 3 illustrates an exemplary interspinous spacer according to one embodiment.

FIG. 3 illustrates an interspinous spacer 50 to stabilize the spine following a laminectomy. In a typical laminectomy, the laminae 22 and spirious process 26 of one or more vertebrae 10 are removed creating a void between remaining superior vertebra and inferior vertebrae 10 adjacent the void. The interspinous spacer 50 shown in FIG. 3 is designed to replace one lamina 22, however, those skilled in the art will recognize that the same design may be used to replace two or more consecutive lamina 22. The interspinous spacer 50 may be secured by pedicles screws 56, tethers 80, or by a combination of pedicle screws 56 and tethers 80.

The interspinous spacer 50 comprises a pair of anchoring plates 52 connected together by a superior arch 60 and an inferior arch 70. The anchoring plates 52 may include an opening 54 to accommodate pedicle screws 56, tethers 80 or other fastening devices for fastening the interspinous spacer 50 to the compromised vertebra 10. The superior arch 60 and inferior arch 70 define a fully enclosed central opening 90. The superior arch 60 and inferior arch 70 each include a saddle indicated respectively at 62 and 72. The saddle 62 in the superior arch 60 receives the spinous process 26 of a superior vertebra 10, while the saddle 72 in the inferior arch 72 receives the spinous process 26 of an inferior vertebra 10. Small passages 64, 74 may be formed in the superior and inferior arches 60, 70 for tethers 80. The engagement of the spinous processes 26 of the superior and inferior vertebra 10 maintains the desired spacing between the superior and inferior vertebrae 10 and prevents compression of the nerve root. The saddles 62, 72 capture the spinous process 26 in a way that allows the spine to flex in the sagittal plane, but limits bending or shifting in the coronal plane. Further, the superior and inferior arches 60, 70 may flex slightly allowing some vertical compression of the interspinous spacer 50.

Figure 12:
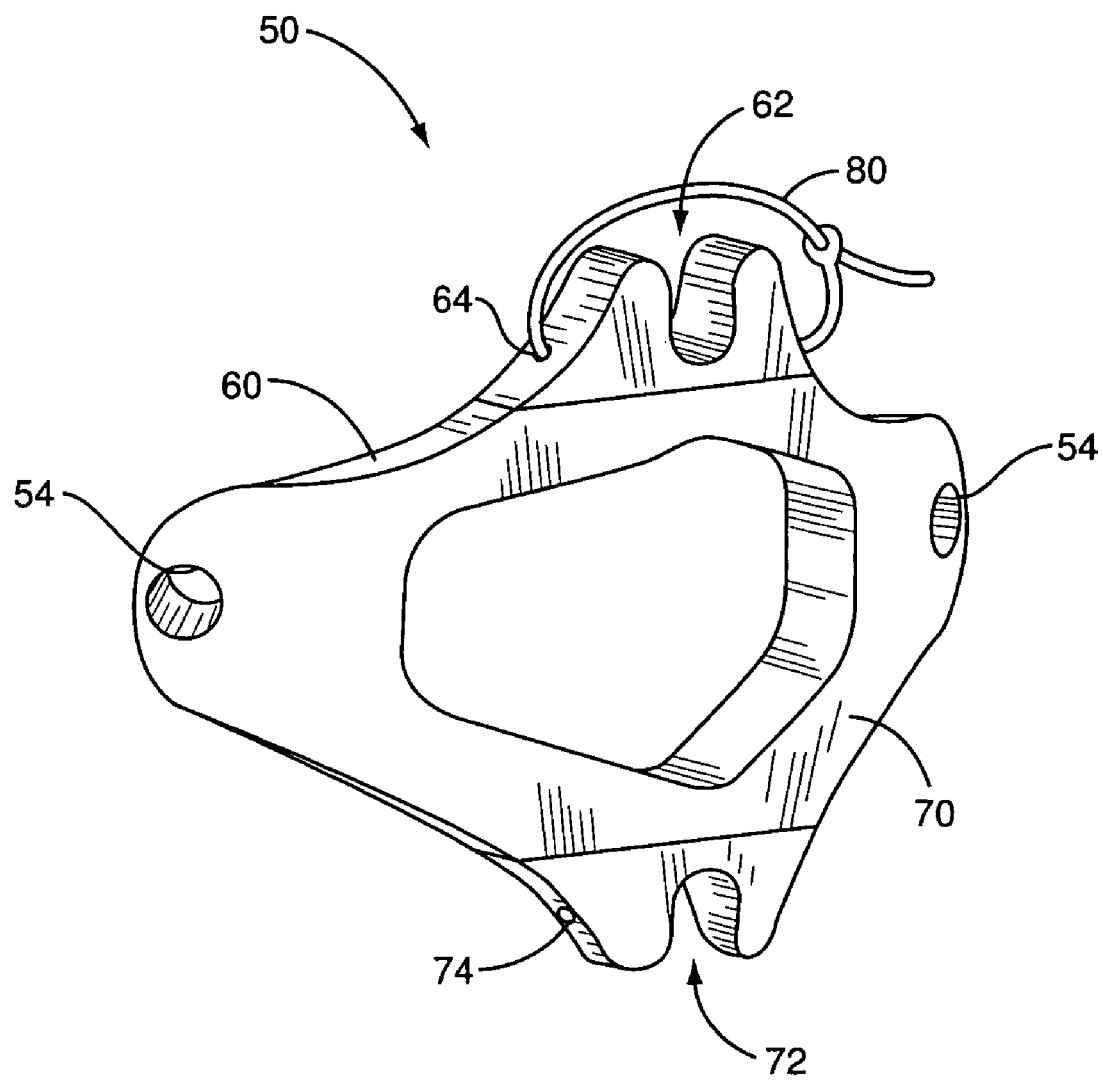
FIG. 12 illustrates an exemplary interspinous spacer according to one embodiment.

In one embodiment, the entire interspinous spacer 50 is a unitary construction made of a rigid or semi-rigid material to stabilize the spine. One suitable material is polyetheretherketone (PEEK), which is a semi-rigid material with some flexibility. In other embodiments, the saddles 62,72 may be constructed as separate components and fastened to the superior and inferior arches 60, 70. For example, the saddles 62, 72 can be made of silicon with a polyethylene cover, and may be mounted to the interspinous spacer 50 as shown in FIG. 12.

Figure 4:
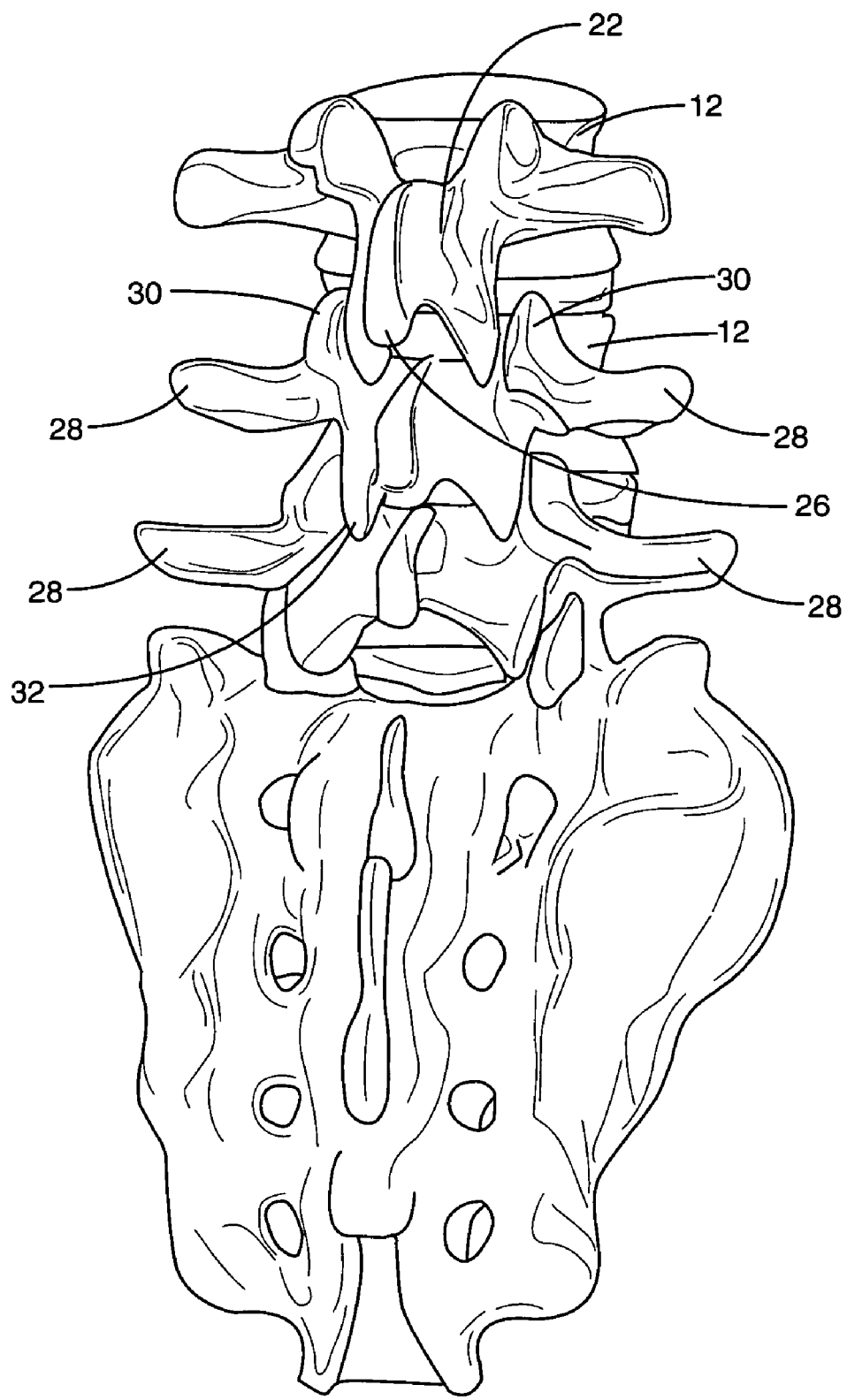
FIGS. 4-8 illustrate a laminectomy procedure using the interspinous spacer shown in FIG. 3.
Figure 5:
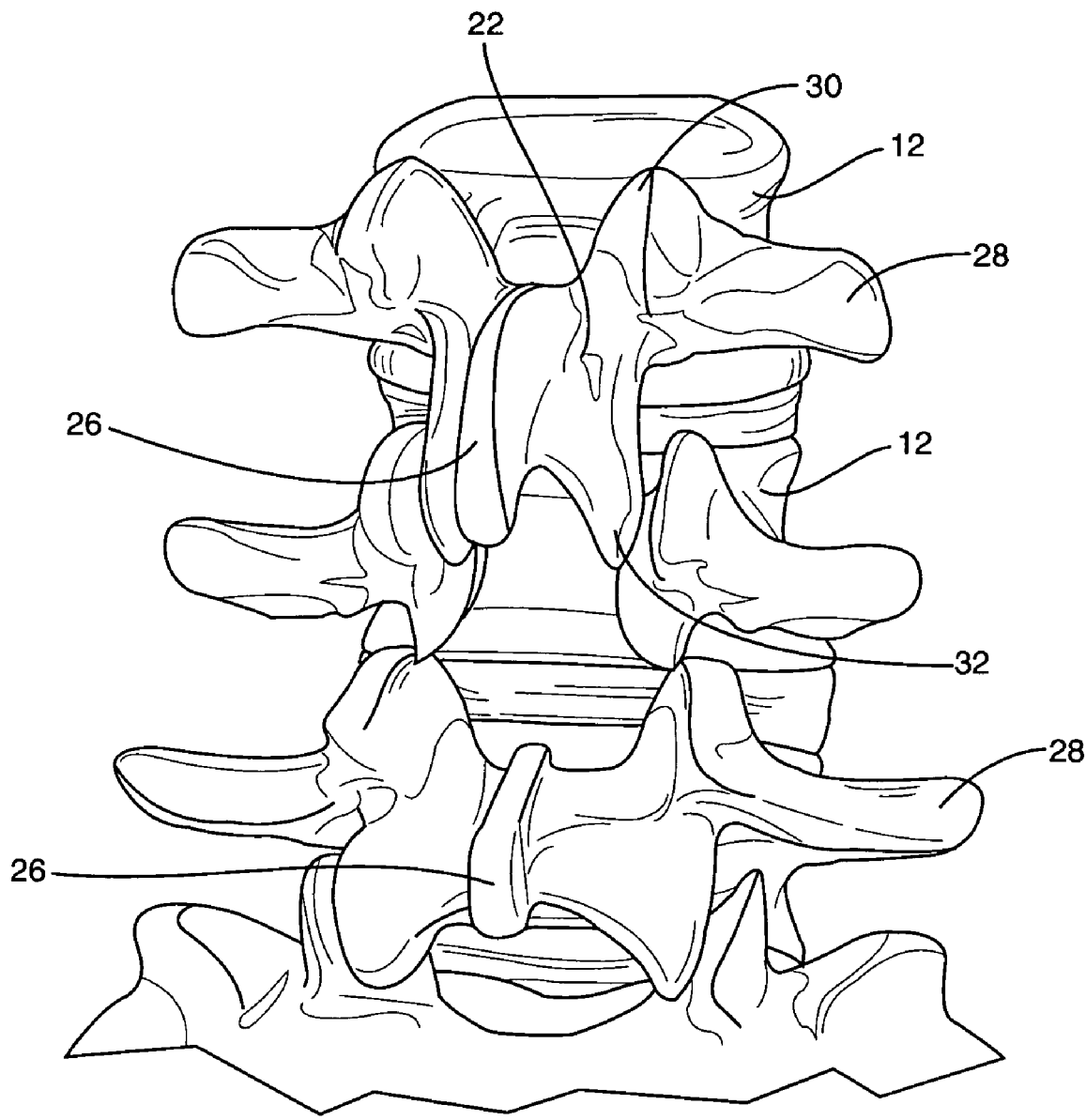
Figure 6:
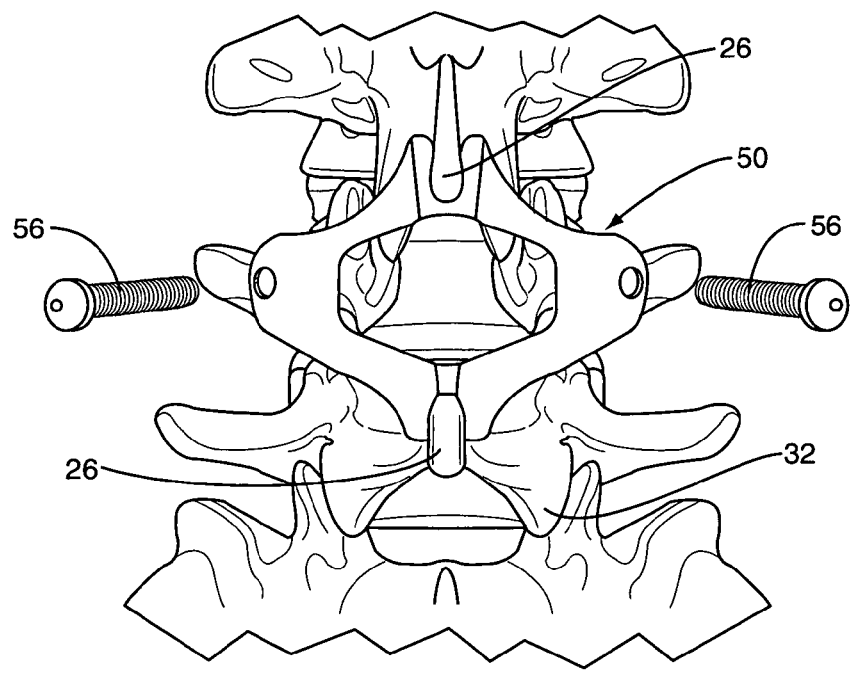
Figure 7:
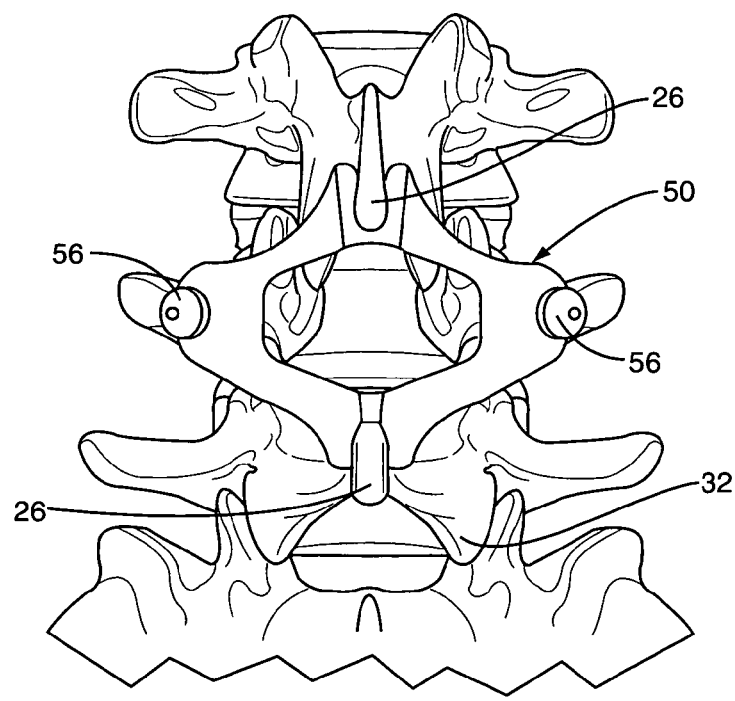
Figure 8:
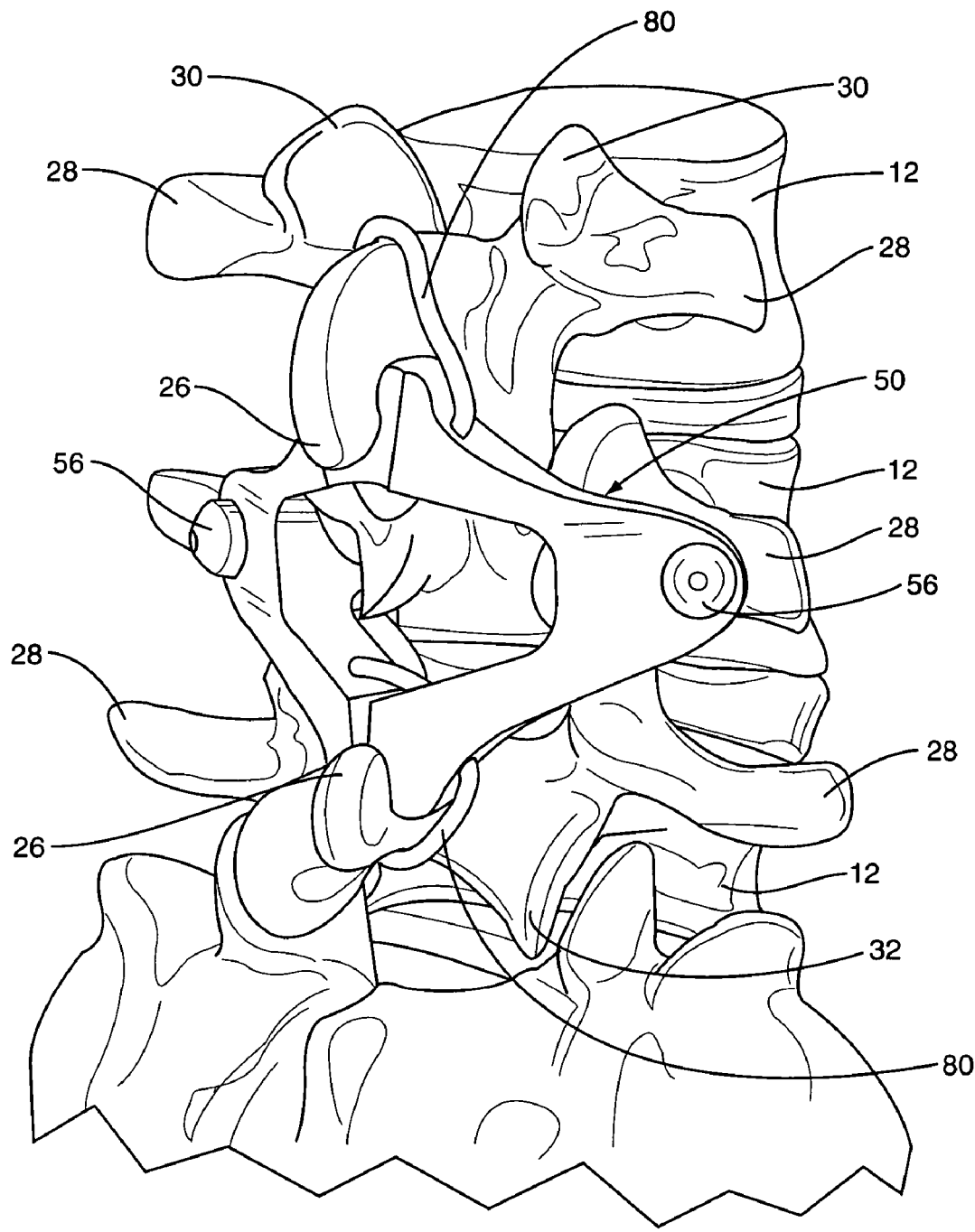

FIGS. 4-8 illustrate steps in a laminectomy procedure using the interspinous spacer 50. FIG. 4 illustrates a portion of the lumbar spine. In this example, the L4 vertebra 10 requires a laminectomy. FIG. 5 illustrates the lumbar spine with the lamina 22 and spinous process 26 of the L4 vertebrae 10 removed creating a void between the L3 and L5 vertebrae 10. With the lamina 22 removed, the spine is unstable. In FIG. 6, the interspinous spacer 50 is positioned between the L3 and L5 vertebrae 10 to maintain decompression of the spinal canal. The saddles 62 and 72 of the superior arch and inferior arch receive, respectively, the spinous processes 26 of the L3 and L5 vertebrae 10. In FIGS. 7 and 8, pedicle screws 56 are inserted through screw holes in the anchor plates 52 to firmly attach the interspinous spacer 50 to the pedicles 20 of the compromised L4 vertebra 10. To complete the procedure, tethers 80 are looped around the spinous processes 26 of the L3 and L5 vertebra 10 to retain the spinous processes 26 in their respective saddles 62, 72 as described in U.S. Pat. No. 6,626,944, which is incorporated herein by reference.

Figure 9A:
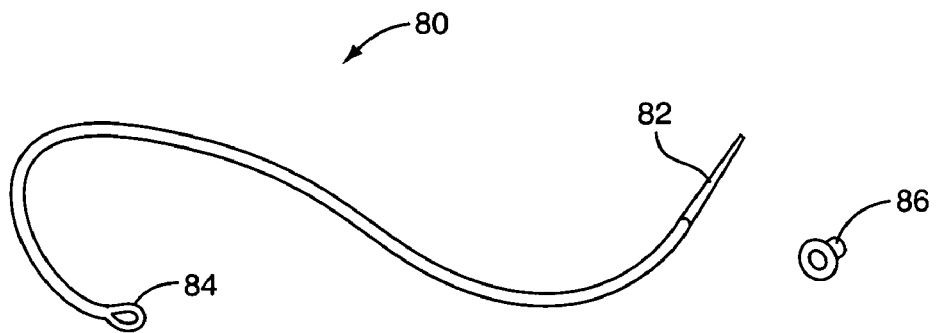
FIGS. 9A-9C illustrate a tether used to secure the interspinous spacer.
Figure 9B:
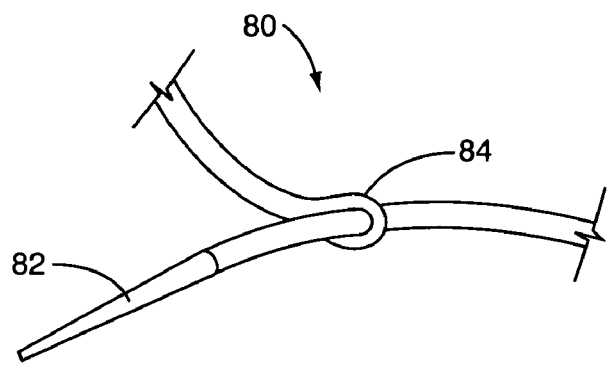
Figure 9C:
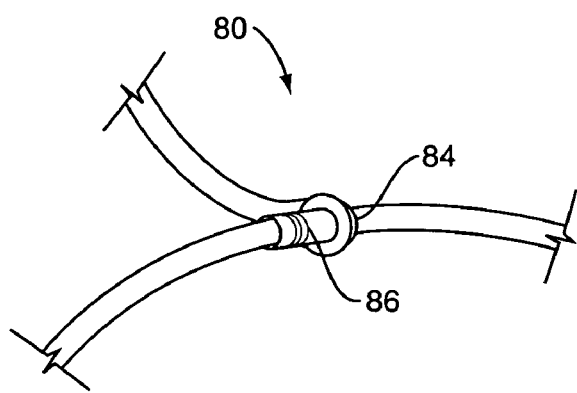

FIGS. 9A-9C illustrates an exemplary tether 80 in more detail. The tether 80 comprises a cord made of polyethylene or other suitable material having a ring 84 at one end and a needle 82 at the opposite end as shown in FIG. 9A. The tether 80 is passed around the spinous process 26 and the needle 82 is then inserted through the ring 84 (FIG. 9B) to form a loop around the spinous process 26. A metallic ferrell 86 slides over the end of the tether 80 and up against the ring 84. The loop is tightened and the ferrell 86 is crimped. The excess cord is then cut flush with the ferrell 86. In some embodiments of the invention, the tether 80 may pass around the superior and inferior arches 62, 72. In other embodiments, the superior and inferior arches 62, 72 may include small passages 64, 74 respectively through which the tether 80 may pass. In other embodiments, the tether 80 may comprise a simple strand or cord that can be looped around the processes and tied at the ends.

Figure 10:
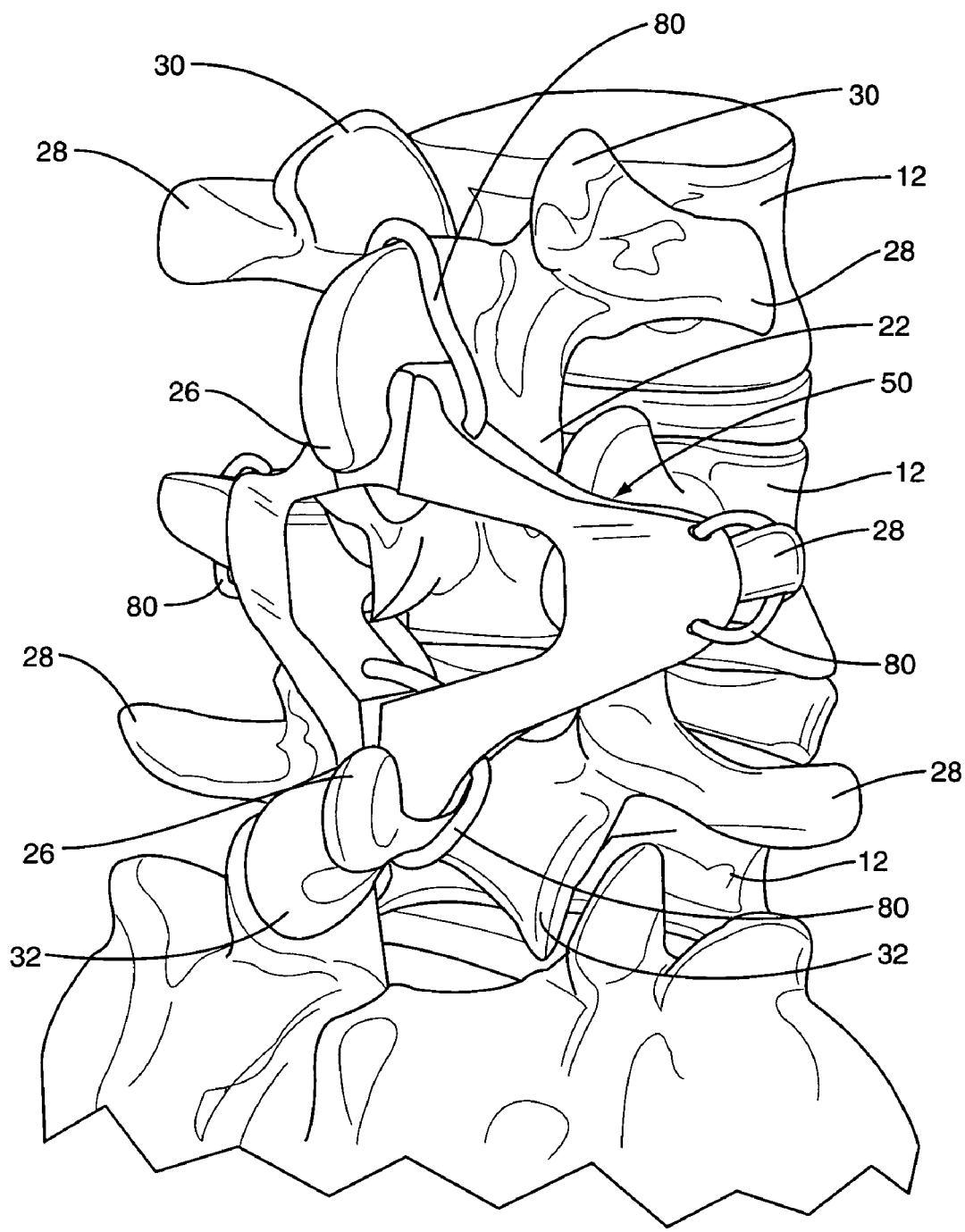
FIG. 10 illustrates an alternate method of securing the interspinous spacer shown in FIG. 3.

FIG. 10 illustrates an alternate method of securing the interspinous spacer 50. As shown in FIG. 10, the interspinous spacer 50 is held in place by two sets of tethers 80. No pedicle screws 56 are used. A first set of tethers 80 pass around the transverse processes 28 of the compromised vertebra 10 and connect the transverse processes 28 to the anchor plates 52. The second set of tethers 80 pass around the spinous processes 26 of the adjacent superior and inferior vertebrae 10 and connect to the superior and inferior vertebrae 10 to the superior and inferior arches 60, 70 respectively.

Figure 11:
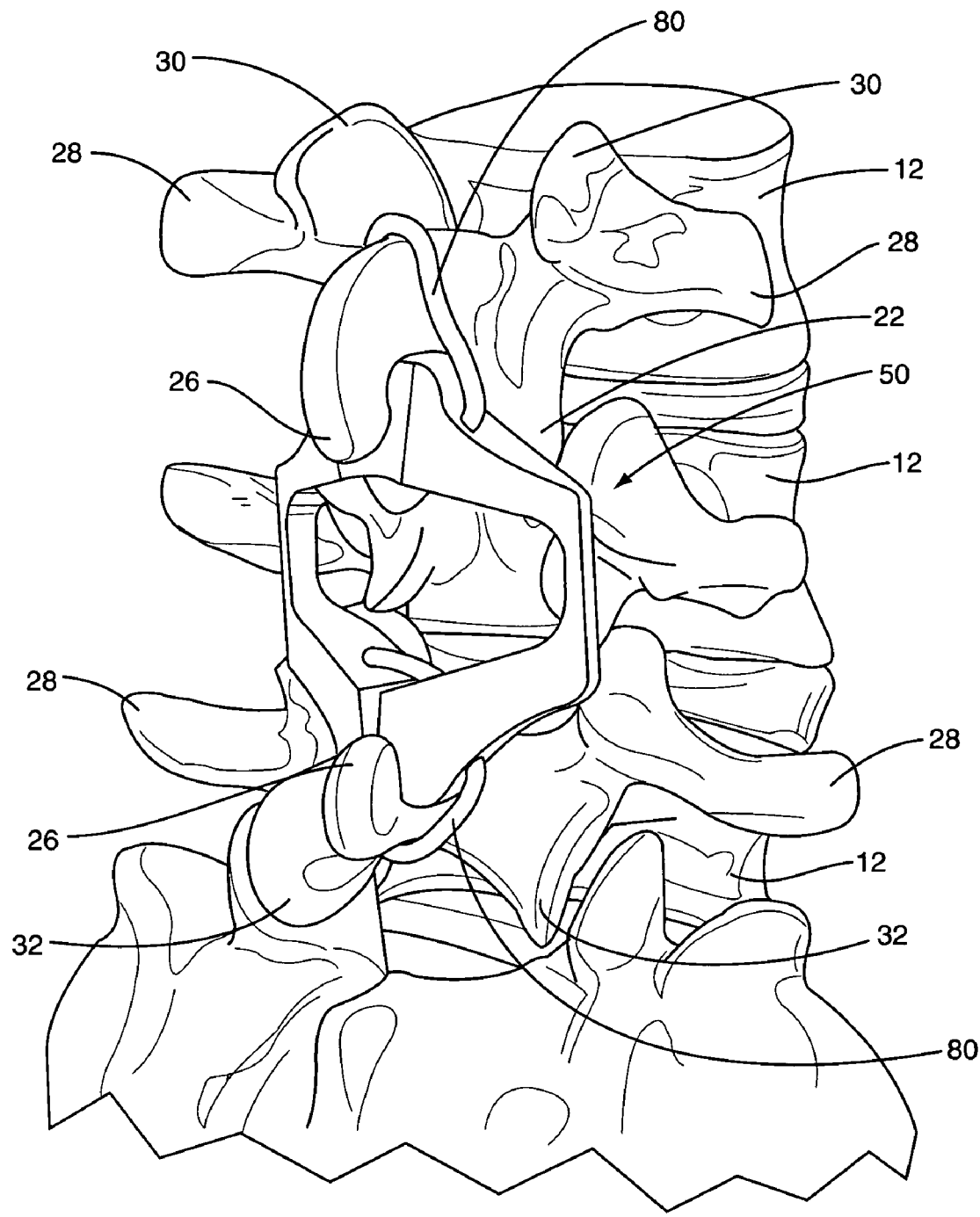
FIG. 11 illustrates an exemplary interspinous spacer according to one embodiment.

FIG. 11 illustrates an alternate embodiment of the interspinous spacer 50. This embodiment is similar to the embodiment shown in FIGS. 1-8. Therefore, the same reference numerals are used to indicate similar components in the two embodiments. The embodiment shown in FIG. 10 comprises a superior arch 60 and an inferior arch 70 without anchoring plates 52. The superior and inferior arches 60, 70 join along a midline of the interspinous spacer 50. The superior arch 60 includes a saddle to receive the spinous process 26 of a superior vertebra 10, while the inferior arch 70 includes a saddle to receive the spinous process 26 of an inferior vertebra 10. The interspinous spacer 50 is held in place by tethers 80 that loop around the spinous processes 26 of the adjacent of the adjacent superior and inferior vertebrae 10 as previously described.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An interspinous spacer comprising:
    anchoring plates for securing the interspinous spacer to a vertebra;
    a superior arch and an inferior arch connecting the anchoring plates and forming a central opening in the interspinous spacer;
    a first saddle disposed on a superior side of the superior arch and centered along the superior arch to capture the spinous process of a superior vertebra;
    a second saddle disposed on an inferior side of the inferior arch and centered along the inferior arch to capture the spinous process of an inferior vertebra; and
    an aperture in each of the anchoring plates being sized to receive a pedicle screw for attaching the interspinous spacer to the pedicles of the vertebra, each of the apertures being laterally aligned with a central section of the central opening;
    the first saddle extends farther in a superior direction than a remainder of the superior arch.

2. The interspinous spacer of claim 1 comprising first and second tethers attached to respective anchoring plates for extending around an adjacent transverse process of the vertebra to secure the interspinous spacer to the vertebra.

3. The interspinous spacer of claim 2 further comprising third and fourth tethers connected to the superior arch and inferior arch respectively for extending around the spinous processes of adjacent vertebrae to retain the spinous processes in their respective saddles.

4. The interspinous spacer of claim 1 further comprising first and second tethers connected to the superior arch and inferior arch respectively for extending around the spinous processes of adjacent vertebrae to retain the spinous processes in their respective saddles.

5. The interspinous spacer of claim 1 wherein the first and second saddles and the superior and inferior arches are formed from one piece.

6. The interspinous spacer of claim 1 made as a unitary one-piece body.

7. The interspinous spacer of claim 1 wherein the superior and inferior arches are made of a semi-rigid but slightly flexible material.

8. An interspinous spacer comprising:
    anchoring plates for securing the interspinous spacer to a vertebra;
    a superior arch and an inferior arch forming a central opening in the interspinous spacer;
    a first saddle positioned at a central region of the superior arch to receive and contact against an inferior edge of the spinous process of a superior vertebra, an entrance into the first saddle positioned in a superior direction beyond the superior arch;
    a second saddle positioned at a central region of the inferior arch to receive and contact against a superior edge of the spinous process of an inferior vertebra, an entrance into the second saddle positioned in an inferior direction beyond the inferior arch; and
    wherein the spacer is made as a unitary one-piece body.

9. The interspinous spacer of claim 8 further comprising first and second tethers connected to the superior arch and inferior arch respectively for extending around the spinous processes of adjacent vertebrae to retain the spinous processes in contact with respective saddles.

10. The interspinous spacer of claim 8 wherein the first and second saddles and the superior and inferior arches are formed from one piece.

11. The interspinous spacer of claim 8 wherein the superior and inferior arches are made of a semi-rigid but slightly flexible material.

12. An interspinous spacer comprising:
- anchoring plates each including an aperture to receive a screw to secure the interspinous spacer to a vertebra;
- a superior arch and an inferior arch forming a central opening in the interspinous spacer, the central opening being sized to create a window, the central opening including open space aligned directly between the apertures to allow visual observation of placement of the apertures relative to the vertebrae, the apertures being aligned with a central section of the central opening;
- each of the superior and inferior arches including a notch extending into a surface of the arches and including opposing sidewalls and a bottom wall sized to capture a superior and inferior spinous processes respectively;
- a first tether extending outward from the superior arch to extend around the superior spinous process that is engaged within the notch in the superior arch;
- a second tether extending outward from the inferior arch to extend around the inferior spinous process that is engaged within the notch in the inferior arch; and
- wherein the superior arch and inferior arch are engageable to the superior and inferior spinous processes respectively to maintain a desired spacing between the superior and inferior vertebrae;
- wherein, when the spacer is in a single given position the apertures are positionable on a first plane that is generally perpendicular to a sagittal plane that extends through the spinous processes and the notches are positionable on a second plane that is generally parallel to and offset in a posterior direction from the first plane.

13. The interspinous spacer of claim 12 wherein the anchoring plates and the superior and inferior arch are made as a unitary one-piece body.

14. The interspinous spacer of claim 12 wherein the superior and inferior arches are made of a semi-rigid but slightly flexible material.

15. A method of stabilizing the spine following a laminectomy, comprising:
- positioning an interspinous spacer including a superior arch and an inferior arch defining a central opening between a superior vertebra and an inferior vertebra adjacent to a compromised vertebra, the central opening including open space aligned directly between attachment apertures;
- visually observing placement of the interspinous spacer and placement of the attachment apertures relative to the superior vertebra and the inferior vertebra through the central opening;
- introducing an inferior edge of a spinous process of the superior vertebra into an opening in a notch included with the superior arch and seating the inferior edge against a contact surface of the notch, the opening extending in a superior direction beyond a remainder of the superior arch to receive the spinous process of the superior vertebra;
- introducing a superior edge of a spinous process of the inferior vertebra into an opening in a notch included with the inferior arch and seating the superior edge against a contact surface of the notch, the opening extending in an inferior direction beyond a remainder of the inferior arch to receive the spinous process of the inferior vertebra;
- extending a first tether outward from the superior arch to extend around the superior spinous process that is engaged within the notch in the superior arch;
- extending a second tether outward from the inferior arch to extend around the inferior spinous process that is engaged within the notch in the inferior arch; and
- maintaining a desired spacing of the superior and inferior vertebrae.

16. The method of claim 15 further comprising extending tethers around transverse processes of the compromised vertebra.

* * * * *